United States Patent [19]

Rauleder et al.

[11] Patent Number: 4,486,606

[45] Date of Patent: Dec. 4, 1984

[54] PROCESS FOR PREPARING PINACOLONE

[75] Inventors: Gebhard Rauleder, Haan; Helmut Waldmann, Leverkusen, both of Fed. Rep. of Germany

[73] Assignee: Bayer Aktiengesellschaft, Leverkusen, Fed. Rep. of Germany

[21] Appl. No.: 477,470

[22] Filed: Mar. 21, 1983

[30] Foreign Application Priority Data

Mar. 26, 1982 [DE] Fed. Rep. of Germany ....... 3211306

[51] Int. Cl.³ ............................................ C07C 45/28
[52] U.S. Cl. ................................................... 568/385
[58] Field of Search ...................... 568/385, 342, 400

[56] References Cited

U.S. PATENT DOCUMENTS

| | | | |
|---|---|---|---|
| 3,803,243 | 9/1974 | Brownstein et al. | 568/385 |
| 3,847,956 | 11/1974 | Silbert et al. | 568/385 |
| 4,000,200 | 12/1976 | Cox | 568/342 |

*Primary Examiner*—James H. Reamer
*Attorney, Agent, or Firm*—Sprung Horn Kramer & Woods

[57] ABSTRACT

Pinacolone is prepared by adding 2,3-dimethyl-2-butene and an aqueous solution of hydrogen peroxide at a temperature of 20° to 90° C. to a solution which contains water and one or more carboxylic acids having 1 to 8 C atoms and which can, if desired, also contain small amounts of a strong acid, increasing the temperature after substantial or complete reaction of the hydrogen peroxide, and distilling off as an azeotropic mixture with water the pinacolone formed.

12 Claims, No Drawings

PROCESS FOR PREPARING PINACOLONE

The present invention relates to a process for preparing pinacolone also called pinacolin in earlier nomenclature, from 2,3-dimethyl-2-butene and hydrogen peroxide in the presence of carboxylic acids.

Pinacolone is a known organic intermediate product which is used in particular for preparing plant protection agents (see, for example, Ullmanns Enzyklopädie der technischen Chemie [Ullmann's Encyclopedia of Industrial Chemistry], 4th edition, volume 14 (1977), page 203).

Japanese Preliminary Published Application No. 56-36,427 (Japanese Patent Application No. 113,199 of Mar. 9, 1979) has already described a process for preparing pinacolone from 2,3-dimethyl-2-butene and hydrogen peroxide in the presence of carboxylic acids and strong inorganic acids. As the example of this Japanese preliminary published application describes in more detail, 30% strength hydrogen peroxide was added at 40° C. to a mixture which contains 1,1,2,2-tetrachloroethane, formic acid, 6.6% by volume, relative to the formic acid, of sulphuric acid, some of the hydrogen peroxide solution to be added and 2,3-dimethyl-2-butene. The mixture was then heated to 60° C. and stirred for a further 3 hours. More than 10 times the weight, relative to the 2,3-dimethyl-2-butene used, of 27% strength sulphuric acid were then added to this mixture, and the resulting mixture was then boiled under reflux for 2 hours. The organic phase was then separated off, washed with 5% strength sodium hydroxide solution and water until neutral, dried with sodium sulphate and distilled. The pinacolone yield was 64%.

A significant disadvantage of this process resides in the large amounts of sulphuric acid which are required. Furthermore, no information is provided about working up the formic acid/sulphuric acid/water mixture and re-using it. However, a direct re-use of this mixture is impossible in any case, since it would otherwise be continually diluted by water added to and formed in the reaction. The carboxylic acid remains in the sulphuric acid solution and would become concentrated there. Finally, the use of an organic solvent, and the associated two-step procedure, is also a disadvantage.

A process has now been found for preparing pinacolone from 2,3-dimethyl-2-butene and hydrogen peroxide in the presence of water, carboxylic acid and, if desired, a strong acid, which is characterised in that 2,3-dimethyl-2-butene and an aqueous solution of hydrogen peroxide are added at a temperature of 20° to 90° C. to a solution which contains water and one or more carboxylic acids having 1 to 8 C atoms and which can, if desired, also contain small amounts of a strong acid, the temperature is increased after substantial or complete reaction of the hydrogen peroxide, and the pinacolone formed is distilled off as an azeotropic mixture with water.

Examples of carboxylic acids which are suitable for use in the process according to the invention are monocarboxylic acids having 1 to 7 C atoms and dicarboxylic acids having 3 to 8 C atoms. Such carboxylic acids may be unsubstituted or substituted. Substituents are preferably those which do not undergo oxidation reactions under reaction conditions, for example fluorine and/or chlorine atoms are suitable substituents. Formic acid, acetic acid, propionic acid, malonic acid, maleic acid, fumaric acid and glutaric acid are preferably used. In general, only one carboxylic acid is used, but it is also possible to use several carboxylic acids.

The amount of water which is initially introduced together with the carboxylic acid(s) can be chosen in such a way, for example, that the carboxylic acid(s) concentration in water is 25 to 85% by weight. This concentration is preferably 30 to 60% by weight.

The concentration of strong acid in the aqueous solution of the carboxylic acid(s) can be, for example, 0 to 30% by weight. If strong carboxylic acids are used, for example maleic acid or fumaric acid, the process according to the invention is preferably carried out in the absence of other strong acids. If carboxylic acids other than maleic acid or fumaric acid are used, the concentration of strong acid is preferably set at 5 to 20% by weight (relative to the total solution initially introduced).

Examples of suitable strong acids are mineral acids, aromatic sulphonic acids and other acids having a pKa-value of less than 3.5. Preferably sulphuric acid or p-toluenesulphonic acid is used, particularly preferably sulphuric acid.

2,3-Dimethyl-2-butene and an aqueous solution of hydrogen peroxide are then added to the mixture of water, carboxylic acid and, if desired, strong acid. In this process, the molar ratio of hydrogen peroxide used to carboxylic acid can be, for example, 0.3:1 to 5:1. The molar ratio is preferably within a range of 0.5:1 to 4:1.

The molar ratio of hydrogen peroxide used to 2,3-dimethyl-2-butene used can be, for example, 0.2:1 to 1.2:1. The molar ratio is preferably within a range of 0.7:1 to 1.15:1, particularly preferably between 1:1 and 1.1:1.

Aqueous hydrogen peroxide solutions of various concentrations are suitable for use in the process according to the invention, for example 30 to 70% by weight, preferably 40 to 60% by weight, aqueous hydrogen peroxide solutions.

The process according to the invention can be carried out under a very wide range of pressures during the addition of hydrogen peroxide and 2,3-dimethyl-2-butene. This pressure is preferably at least sufficiently high to stop significant amounts of the reaction mixture from evaporating. The temperature during the addition of 2,3-dimethyl-2-butene and aqueous hydrogen peroxide is within a range of 20° to 90° C. This temperature is preferably within a range of 30° to 65° C. At the preferable reaction temperature the reaction can be carried out under normal pressure. Temperatures within a range of 50° to 65° C. and normal pressure are particularly preferable.

Examples of materials of which the reaction units for carrying out the process according to the invention can be constructed are glass, stainless steels and enamelled material.

Apart from working under isothermal conditions, that is apart from maintaining a uniform temperature during and after the addition of 2,3-dimethyl-2-butene and aqueous hydrogen peroxide, the process according to the invention can also be carried out by forming a so-called temperature gradient, which generally increases as the addition of 2,3-dimethyl-2-butene and aqueous hydrogen peroxide proceeds. However, the reaction can also be carried out in such a way that a decreasing temperature gradient forms as the reaction proceeds.

When the addition of aqueous hydrogen peroxide and 2,3-dimethyl-2-butene is complete, it is generally necessary to keep the reaction mixture, preferably with stirring, for some more time at the reaction temperature until the hydrogen peroxide has substantially or completely reacted. As soon as it is found, for example by appropriate analysis, that hydrogen peroxide conversion has reached a value of, for example, above 90%, preferably above 95%, the temperature is increased and the pinacolone formed is distilled off as an azeotropic mixture with water. In this distillation, acetone and/or dimethylbutadiene which have been formed as by-products may pass over at the top.

The mixture which stays behind when this azeotropic distillation is complete and which essentially contains the carboxylic acid used and water and which can, if desired, also contain the strong acid used can be used directly in a new reaction cycle in which 2,3-dimethyl-2-butene and aqueous $H_2O_2$ are again added to it under the conditions according to the invention.

Pinacolone can be isolated from the mixture obtained as the top product in the azeotropic distillation by separating off water in a water separator after its condensation and obtaining pinacolone by redistillation from the remaining organic phase. The azeotropic distillation is generally carried out under normal pressure. However, it can also be carried out under elevated or reduced pressure.

The process according to the invention has a particular advantage in that, after pinacolone and water have been distilled off, the remaining mixture of carboxylic acid, water and, if desired, strong acid remains in the reactor and can be used directly, without further measures, for a new batch. Also, unlike the state of the art, the process according to the invention does not require organic solvent and, if at all, significantly smaller amounts of strong acid.

It is very surprising that, nevertheless, the process according to the invention can produce pinacolone in virtually the same yields as the state of the art.

EXAMPLES

EXAMPLE 1

116 g of maleic acid (1 mol) and 200 g of water were initially introduced into a 1 liter double-walled flask equipped with a stirrer and a distillation attachment, and thermostated to 65° C. 76 g of 2,3-dimethyl-2-butene (0.9 mol) and 68 g of 50% strength aqueous hydrogen peroxide (1 mol) were metered in with stirring and under normal pressure via separate lines by means of diaphragm pumps in the course of 1.75 hours. After the metering-in was complete, the mixture was stirred for a further 4 hours at this temperature. At this point, the degree of hydrogen peroxide conversion was 95%. The temperature was then increased and the pinacolone formed was distilled off under normal pressure together with water, acetone and dimethylbutadiene. An internal temperature of 95° to 102° C. became established in this distillation. After the aqueous phase had been separated off, the organic mixture was distilled again. This produced pinacolone in a yield of 56 g, which corresponds to 62.2% of theory.

EXAMPLE 2

The aqueous maleic acid remaining in the reactor in Example 1 was again reacted with the amounts of 2,3-dimethyl-2-butene and 50% strength hydrogen peroxide specified in Example 1, and the reaction product was worked up as described in Example 1. Pinacolone was again obtained in a yield of 62% of theory. This experimental sequence was repeated a total of ten times. Even after the tenth repetition, the pinacolone yield remained virtually unchanged, at 61%.

EXAMPLE 3

23 g of formic acid (0.5 mol), 47 g of water and 10 g of concentrated sulphuric acid were initially introduced into a reactor of the type described in Example 1, and thermostated to 65° C. 168 g of 2,3-dimethyl-2-butene (2 mols) and 136 g of 50% strength hydrogen peroxide (2 mols) were then metered in in the course of 3.5 hours in the way described in Example 1. The mixture was then stirred for a further 3 hours at 65° C. The degree of $H_2O_2$ conversion was then 98%. The temperature was then increased and the reaction products distilled off under normal pressure together with water. Working up as described in Example 1 produced pinacolone in a yield of 124 g, which corresponds to 62% of theory.

EXAMPLE 4

84 g of 2,3-dimethyl-2-butene (1 mol) and 68 g of 50% strength hydrogen peroxide (1 mol) were metered in at 65° C. in the course of 1.75 hours into a solution of 30 g of acetic acid (0.5 mol), 50 g of water and 10 g of concentrated sulphuric acid, in the way described in Example 1. After the mixture had been stirred at 65° C. for a further 3 hours, the degree of hydrogen peroxide conversion was 98%. The temperature was then increased and the reaction products distilled off as described in Example 1. Renewed distillation of the organic phase gave 120 g of pinacolone, which corresponds to a yield of 60% of theory.

What is claimed is:

1. In a process for preparing pinacolone by contacting 2,3-dimethyl-2-butene with hydrogen peroxide in the presence of water and an acid, the improvement wherein as the sole acid there is employed maleic acid or fumaric acid or a mixture thereof and the process is conducted at a temperature of 20° to 90° C. and after substantial reaction of the hydrogen peroxide, the temperature is increased and pinacolone formed is azeotropically distilled off with water.

2. A process according to claim 1 wherein the reaction mixture is substantially free of an inorganic acid.

3. A process according to claim 2 wherein the reaction mixture is substantially free of an organic solvent.

4. A process according to claim 3 wherein the maleic acid, fumaric acid or mixture thereof is present in the form of an aqueous solution wherein the combined amount of maleic and fumaric acid is 25 to 85 percent by weight of the resultant aqueous solution.

5. A process according to claim 1, wherein the molar ratio of hydrogen peroxide to a combined amount of maleic and fumaric acid is 0.3 to 5.1.

6. A process according to claim 1, wherein the molar ratio of hydrogen peroxide to 2,3-dimethyl-2-butene is 0.2 to 1.2:1.

7. A process according to claim 1, wherein the process is conducted at a temperature in the range of 30° to 65° C. under normal pressure.

8. A process according to claim 1, wherein after the addition of hydrogen peroxide and 2,3-dimethyl-2-butene is complete, the reaction mixture is maintained at the reaction temperature until at least 90% of the hydrogen peroxide has reacted.

9. A process according to claim 1, wherein the pinacolone formed is azeotropically distilled off with water under normal pressure.

10. A process according to claim 1, wherein, in the azeotropic distillation, the top product is condensed, water is separated off in a water separator and pinacolone is obtained by redistallation in the remaining organic phase.

11. A process according to claim 1, wherein the product which remains in the reactor following azeotropic distillation of pinacolone and water is reused for pinacolone synthesis by the addition of 2,3-dimethyl-2-butene and hydrogen peroxide to such product.

12. A process according to claim 11, wherein the process is carried out in the absence of an organic solvent.

* * * * *